United States Patent
Thornton et al.

(10) Patent No.: US 7,174,895 B2
(45) Date of Patent: Feb. 13, 2007

(54) DEVICE AND METHOD FOR IMPROVING A USER'S BREATHING

(75) Inventors: W. Keith Thornton, 5524 Edlen Dr., Dallas, TX (US) 75220-2106; Michael J. Zalta, Richardson, TX (US)

(73) Assignee: W. Keith Thornton, Dallas, TX (US)

( * ) Notice: Subject to any disclaimer, the term of this patent is extended or adjusted under 35 U.S.C. 154(b) by 65 days.

(21) Appl. No.: 10/428,904

(22) Filed: May 1, 2003

(65) Prior Publication Data

US 2003/0217753 A1    Nov. 27, 2003

Related U.S. Application Data

(60) Provisional application No. 60/376,746, filed on May 1, 2002.

(51) Int. Cl.
*A61F 5/56* (2006.01)
*A61F 11/00* (2006.01)
*A61C 5/14* (2006.01)
*A61C 3/00* (2006.01)

(52) U.S. Cl. ............... 128/848; 128/857; 128/859; 128/861; 433/19

(58) Field of Classification Search .......... 128/848, 128/857, 859, 860, 861, 863, 206.29, 200.26, 128/200.24, 898; 433/6, 19, 42, 215
See application file for complete search history.

(56) References Cited

U.S. PATENT DOCUMENTS

| 690,663 A | 1/1902 | Pratt |
|---|---|---|
| 746,869 A | 12/1903 | Moulton |
| 774,446 A | 11/1904 | Moulton |
| 885,196 A | 4/1908 | Steil |
| 893,213 A | 7/1908 | Whiteway |
| 1,076,534 A | 10/1913 | Wallen |
| 1,146,264 A | 7/1915 | Kelly |
| 1,483,694 A | 2/1924 | Stukey |
| 1,649,664 A | 11/1927 | Carter |
| 1,674,336 A | 6/1928 | King |

(Continued)

FOREIGN PATENT DOCUMENTS

AU    78762/94    4/1995

(Continued)

OTHER PUBLICATIONS

Mayo Clinic Health Letter, vol. 13, No. 7, "Snoring." Jul. 1995.

(Continued)

*Primary Examiner*—Henry Bennett
*Assistant Examiner*—Annette Dixon
(74) *Attorney, Agent, or Firm*—Baker Botts L.L.P.

(57) ABSTRACT

In one embodiment, a device for improving a user's breathing includes an upper arch adapted to receive at least some of the user's upper teeth and a lower arch adapted to receive at least some of the user's lower teeth. A hook having a substantially rounded end is coupled to the upper arch. The lower arch includes a substantially rounded recess adapted to receive and position the substantially rounded end of the hook to pull the lower arch forward to facilitate improved breathing.

57 Claims, 6 Drawing Sheets

U.S. PATENT DOCUMENTS

| | | | |
|---|---|---|---|
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,854,208 A | 12/1974 | Arant | 32/19 |
| 3,864,832 A | 2/1975 | Carlson | 128/136 |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205 |
| 4,289,127 A | 9/1981 | Nelson | 128/207.14 |
| 4,304,227 A | 12/1981 | Samelson | 128/136 |
| 4,345,592 A | 8/1982 | Giorgini et al. | 128/204 |
| 4,345,593 A | 8/1982 | Sullivan | 128/204 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,606 A | 8/1989 | Hamlin | 128/204 |
| 4,862,903 A | 9/1989 | Campbell | 128/861 |
| 4,870,962 A | 10/1989 | Sitnik | 128/205 |
| 4,886,056 A | 12/1989 | Simpson | 128/201 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,064,371 A | 11/1991 | Smeltzer | 433/37 |
| 5,065,756 A | 11/1991 | Rapoport | 128/204 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204 |
| 5,213,498 A | 5/1993 | Pelerin | 433/37 |
| 5,243,971 A | 9/1993 | Sullivan et al. | 128/205 |
| 5,245,995 A | 9/1993 | Sullivan et al. | 128/204 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A * | 11/1994 | Halstrom | 128/848 |
| 5,370,533 A | 12/1994 | Bushnell | 433/36 |
| 5,373,859 A | 12/1994 | Forney | 128/846 |
| 5,409,017 A * | 4/1995 | Lowe | 128/848 |
| 5,415,544 A | 5/1995 | Oxman et al. | 433/48 |
| 5,427,117 A * | 6/1995 | Thornton | 128/848 |
| 5,456,264 A | 10/1995 | Series et al. | 128/725 |
| 5,458,137 A | 10/1995 | Axe et al. | 128/204 |
| 5,477,850 A | 12/1995 | Zegler et al. | 128/202 |
| 5,503,146 A | 4/1996 | Froehlich et al. | 128/204 |
| 5,503,552 A | 4/1996 | Diesso | 433/37 |
| 5,517,983 A | 5/1996 | Deighan et al. | 128/204 |
| 5,537,994 A * | 7/1996 | Thornton | 128/204.18 |
| 5,537,999 A | 7/1996 | Dearman et al. | 128/205 |
| 5,538,000 A | 7/1996 | Rudolph | 128/205 |
| 5,551,419 A | 9/1996 | Froehlich et al. | 128/204 |
| 5,551,872 A | 9/1996 | Mena | 433/37 |
| 5,558,090 A | 9/1996 | James | 128/207.18 |
| RE35,339 E | 10/1996 | Rapoport | 128/204 |
| 5,560,354 A | 10/1996 | Berthon-Jones et al. | 128/205 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,592,935 A | 1/1997 | Elstran et al. | 128/205 |
| 5,611,485 A | 3/1997 | Davis | 239/8 |
| 5,657,751 A | 8/1997 | Karr, Jr. | 128/205 |
| 5,657,752 A | 8/1997 | Landis et al. | 128/207 |
| 5,676,133 A | 10/1997 | Hickle et al. | 128/205 |

| | | | | |
|---|---|---|---|---|
| 5,678,567 A | 10/1997 | Thornton et al. ............ 128/848 | WO WO 98/20924 | 5/1998 |
| 5,681,164 A * | 10/1997 | Bass ............................. 433/6 | WO WO 98/26736 | 6/1998 |
| 5,687,715 A | 11/1997 | Landis et al. .......... 128/207.18 | WO WO 98/46177 | 10/1998 |
| 5,713,349 A | 2/1998 | Keaney ...................... 128/204 | | |
| 5,718,244 A | 2/1998 | Thornton .................... 128/864 | | |
| 5,718,500 A | 2/1998 | Vinci Guerra et al. .......... 2/431 | | |
| 5,720,280 A | 2/1998 | Elstran et al. .............. 128/205 | | |
| 5,720,302 A | 2/1998 | Belfer ................... 128/201.26 | | |
| 5,746,201 A | 5/1998 | Kidd .......................... 128/206 | | |
| 5,752,510 A | 5/1998 | Goldstein ................... 128/207 | | |
| 5,755,219 A * | 5/1998 | Thornton ............... 128/201.18 | | |
| 5,807,100 A | 9/1998 | Thornton ...................... 433/48 | | |
| 5,829,441 A | 11/1998 | Kidd et al. ................. 128/848 | | |
| 5,846,082 A | 12/1998 | Thornton .................... 433/215 | | |
| 5,887,587 A | 3/1999 | Groenke ..................... 128/207 | | |
| 5,954,048 A * | 9/1999 | Thornton ............... 128/201.18 | | |
| 5,983,892 A * | 11/1999 | Thornton ............... 128/201.26 | | |
| 5,988,166 A | 11/1999 | Hayek ........................ 128/205 | | |
| 6,012,455 A | 1/2000 | Goldstein ................... 128/207 | | |
| 6,155,262 A | 12/2000 | Thornton .................... 128/859 | | |
| 6,209,542 B1 * | 4/2001 | Thornton ............... 128/206.29 | | |
| 6,247,926 B1 | 6/2001 | Thornton ...................... 433/48 | | |
| 6,263,871 B1 * | 7/2001 | Brown et al. .......... 128/200.29 | | |
| 6,305,376 B1 | 10/2001 | Thornton .................... 128/848 | | |
| 6,325,064 B1 * | 12/2001 | Thornton .................... 128/848 | | |
| 6,374,824 B1 * | 4/2002 | Thornton ............... 128/201.26 | | |
| 6,405,729 B1 | 6/2002 | Thornton .................... 128/848 | | |
| 6,464,924 B1 | 10/2002 | Thornton ............... 264/331.12 | | |
| 6,516,805 B1 * | 2/2003 | Thornton .................... 128/848 | | |
| 6,571,798 B1 | 6/2003 | Thornton ............... 128/206.21 | | |
| 6,845,774 B2 * | 1/2005 | Gaskell ....................... 128/848 | | |
| 6,877,513 B2 * | 4/2005 | Scarberry et al. ........... 128/848 | | |
| 2001/0047805 A1 * | 12/2001 | Scarberry et al. ...... 128/206.29 | | |
| 2002/0000230 A1 | 1/2002 | Gaskell ....................... 128/848 | | |
| 2004/0237965 A1 * | 12/2004 | Bibi et al. ............. 128/206.29 | | |

FOREIGN PATENT DOCUMENTS

| | | |
|---|---|---|
| AU | 27647/95 | 1/1996 |
| DE | 156627 | 12/1904 |
| DE | 2320501 | 11/1974 |
| DE | 3543931 | 6/1987 |
| DE | 3707952 | 9/1988 |
| DE | 3719009 | 12/1988 |
| DE | 29506512 | 7/1995 |
| DE | 19524534 | 5/1996 |
| EP | 0312368 | 4/1989 |
| EP | 0359135 | 3/1990 |
| GB | 1569129 | 6/1980 |
| WO | WO 91/2777 | 9/1991 |

OTHER PUBLICATIONS

Photocopies of 2-piece dental device manufactured by Currie-Gibson Dental Laboratory, Inc. prior to Apr. 13, 1993.

Farrar & McCarty, "A Clinical Outline of Temporomandibular Joint Diagnosis and Treatment," Normandie Study Group for TMJ Dysfunction, 3 pages, 1983.

Professional Positioners brochure, "Dedicated to Excellence," 4 pages, unknown.

Great Lakes Orthodontics, Ltd., "Nocturnal Airwa Patency Appliance™ (NAPA)," General Instructions, 2 pages, Not Dated.

Schmidt-Nowara, et al., "Oral Appliances for the Treatment of Snoring and Obstructive Sleep Apnea: A Review," Sleep, 18(6):501-510, 1995.

George, "Treatment of Snoring and Obstructive Sleep Apnea with a Dental Device," General Denistry, 5 pages, Jul.-Aug. 1993.

Database WOI, Section PQ, Week 9039, Derwent Publications, Ltd., London, GB XP-002116355—Abstract "Surgical Mouth Air Duct,", Dec. 15, 1989.

CPAP/PRO® . . . Introducting a New Cmfort Level for CPAP Users!! brochure, 2 pages, Undated.

PCT International Search Report, PCT/US97/08708, 4 pages, Aug. 12, 1997.

PCT, International Searching Authority, PCT/US03/13705, 5 pages, Oct. 10, 2003.

W. Keith Thornton and Andrew O. Jamieson, "Method and Apparatus for Adjusting a Dental Device," U.S. Appl. No. 08/218,719, abandoned, Mar. 24, 1994.

W. Keith Thornton, "Apparatus for Prevention of Snoring and Improved Breathing During Sleep," U.S. Appl. No. 08/363,639, abandoned, Dec. 24, 1994.

W. Keith Thornton and Andrew O. Jamieson, "Method and Apparatus for Adjusting a Dental Device," U.S. Appl. No. 08/435,277, abandoned, May 5, 1995.

W. Keith Thornton, "Device for Improving Breathing," U.S. Appl. No. 08/582,526, abandoned, Jan. 3, 1996.

W. Keith Thornton, "Method and Apparatus for Adjusting a Dental Device," U.S. Appl. No. 08/787,529, abandoned, Jan. 21, 1997.

W. Keith Thornton, "Custom Mask and Method of Forming Same," U.S. Appl. No. 09/543,397, abandoned, Apr. 5, 2000.

W. Keith Thornton, "Custom Mask Assembly and Method for Making Same," U.S. Appl. No. 09/543,398, abandoned, Apr. 5, 2000.

W. Keith Thornton, "Device and Method for Improving a User's Breathing," U.S. Appl. No. 09/764,623, abandoned, Jan. 17, 2001.

* cited by examiner

DEVICE AND METHOD FOR IMPROVING A USER'S BREATHING

RELATED APPLICATIONS

This application claims the benefit under 35 U.S.C. §119(e) of U.S Provisional Application Ser. No. 60/376,746, filed May 1, 2002.

TECHNICAL FIELD OF THE INVENTION

This invention relates generally to oral appliances, and more particularly to a device and method for improving a user's breathing.

BACKGROUND

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the breathing passageway more fully to allow easier breathing through the nose and mouth. Certain of these devices include upper and lower arches that are connected together using a mechanism that may be adjusted to pull the lower arch, and thus the user's lower jaw, forward.

SUMMARY OF THE INVENTION

The device and method of the present invention may reduce or eliminate certain disadvantages and problems associated with previous devices and methods for improving breathing.

In one embodiment, a device for improving a user's breathing includes an upper arch adapted to receive at least some of the user's upper teeth and a lower arch adapted to receive at least some of the user's lower teeth. A hook having a substantially rounded end is coupled to the upper arch. The lower arch includes a substantially rounded recess adapted to receive and position the substantially rounded end of the hook to pull the lower arch forward to facilitate improved breathing.

In another embodiment, a hook for a device for improving a user's breathing is adapted to be coupled to an upper arch of the device for receiving at least some of the user's upper teeth. The hook includes a substantially rounded end adapted to be received and positioned within a substantially rounded recess of a lower arch of the device for receiving at least some of the user's lower teeth to pull the upper arch forward to facilitate improved breathing.

In another embodiment, a lower platform for a device for improving a user's breathing is adapted to be coupled to a lower arch of the device that is adapted to receive at least some of the user's lower teeth. The lower platform includes a substantially rounded recess adapted to receive and position a substantially rounded end of a hook coupled to an upper arch of the device to pull the lower arch forward to facilitate improved breathing.

In another embodiment, an upper platform for a device for improving a user's breathing is adapted to be coupled to an upper arch of the device that is adapted to receive at least some of the user's upper teeth. The upper platform includes a slot adapted to receive and engage a flange of a hook. The slot is further adapted to permit forward and rearward travel of the hook within the slot and to substantially prevent lateral and vertical movement of the hook relative to the upper platform. The upper platform also includes a first channel adapted to receive a threaded adjustor that is adapted to engage a second threaded channel formed in the hook such that rotation of the adjustor causes the hook to travel forwardly or rearwardly within the slot. The upper platform further includes a stop at each end of the first channel. The stops are adapted to substantially prevent the adjustor from moving forwardly and rearwardly within the first channel.

In another embodiment, an adjustment mechanism for a device for improving a user's breathing is provided for adjusting a lower arch that is adapted to receive at least some of a user's lower teeth. The adjustment mechanism includes a hook having a substantially rounded end and an upper platform having a slot adapted to receive and engage a flange of the hook. The slot is further adapted to permit forward and rearward travel of the hook within the slot and to substantially prevent lateral and vertical movement of the hook relative to the upper platform. In addition, the adjustment mechanism includes a threaded adjustor disposed in a first channel formed in the upper platform. The adjustor is adapted to engage a second threaded channel formed in the hook such that rotation of the adjustor causes the hook to travel forwardly and rearwardly within the slot.

In another embodiment, a positioning mechanism for a device for improving a user's breathing is provided for positioning a lower arch that is adapted to receive at least some of a user's lower teeth. The positioning mechanism includes a hook adapted to be coupled to an upper arch that is adapted to receive at least some of the user's upper teeth. The hook includes a substantially rounded end. The positioning mechanism also includes a lower platform adapted to be coupled to the lower arch. The lower platform includes a substantially rounded recess adapted to receive and position the substantially rounded end of the hook to pull the lower arch forward to facilitate improved breathing.

In yet another embodiment, a method for improving a user's breathing includes inserting into the user's mouth an upper arch that is adapted to receive at least some of the user's upper teeth. The upper arch is coupled to a hook having a substantially rounded end. A lower arch is inserted into the user's mouth, the lower arch being adapted to receive at least some of the user's lower teeth. The lower arch includes a substantially rounded recess adapted to receive and position the substantially rounded end of the hook to pull the lower arch forward to facilitate improved breathing. The substantially rounded end of the hook is positioned in the substantially rounded recess of the lower arch and the hook is adjusted while the upper and lower arches are in the user's mouth to pull the lower arch forward to facilitate improved breathing.

Certain embodiments of the present invention may provide one or more technical advantages. For example, certain embodiments may allow the lower arch to be precisely positioned relative to the upper arch, while still allowing certain freedom of movement of the lower jaw. As another example, certain embodiments may allow the lower arch to be precisely positioned vertically relative to the upper arch to precisely determine the opening of the user's lower jaw. As another example, in certain embodiments the device, including a positioning mechanism, an adjustment mechanism, or both, may reside entirely within the user's mouth for improved comfort and usability. Certain embodiments may provide all, some, or none of these advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and at least some of its advantages, reference is now made to the following description taken in conjunction with the accompanying drawings, in which.

DESCRIPTION OF EXAMPLE EMBODIMENTS

Figure 1:
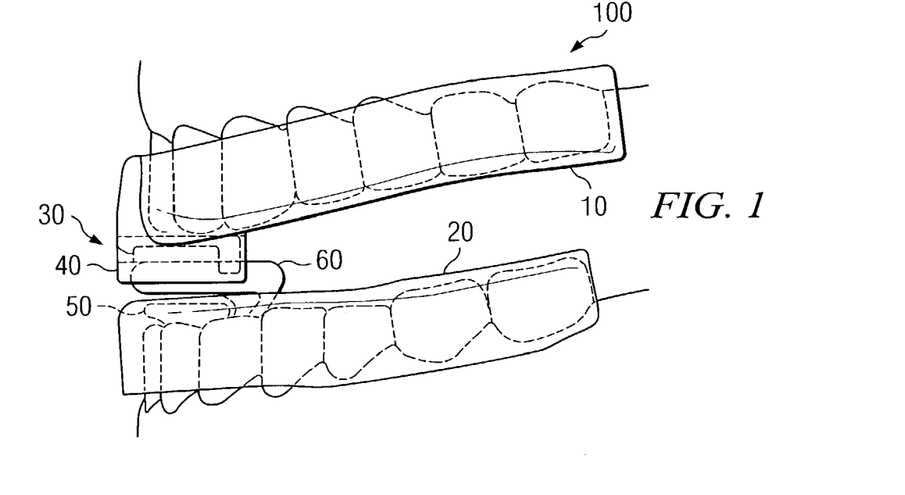
FIG. 1 illustrates a device for improving a user's breathing.
Figure 2:
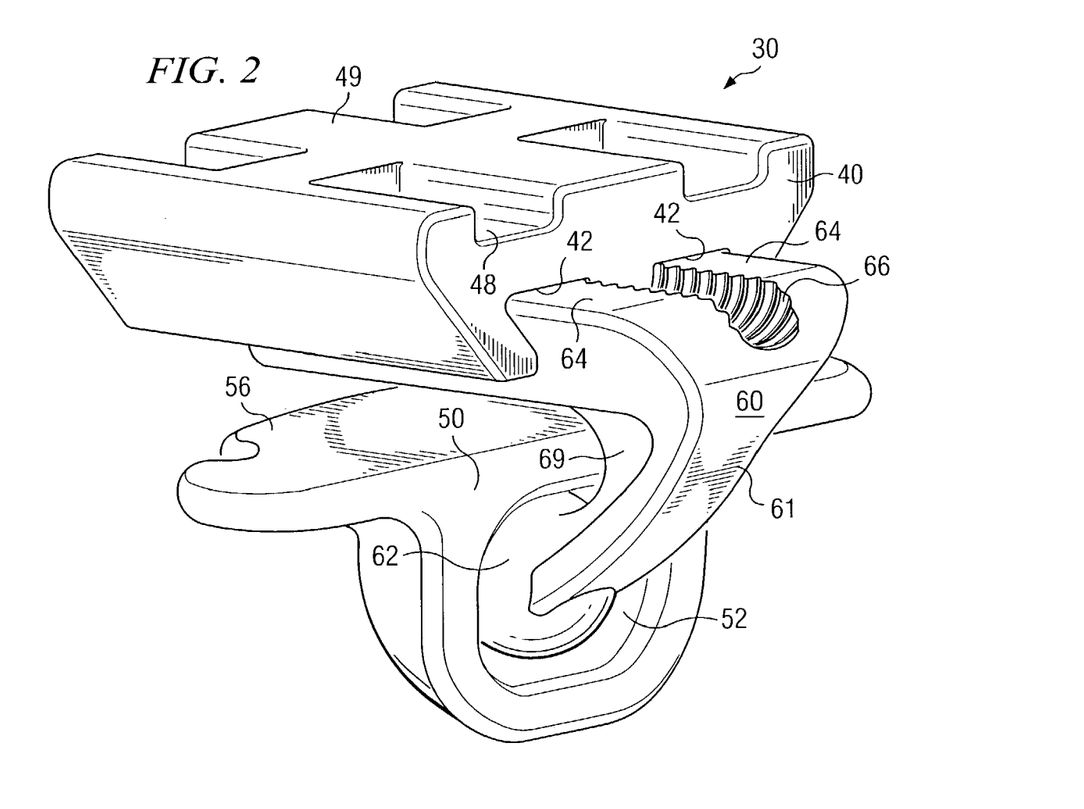
FIGS. 2 through 5 illustrate more detailed views of example vertical positioning and forward adjustment mechanisms.

FIG. 1 illustrates an example device 100 for improving a user's breathing. In general, device 100 may be used to treat sleep disordered breathing, such as snoring or obstructive sleep apnea, through forward adjustment of the user's lower jaw relative to the upper jaw. This opens the breathing passage and facilitates improved breathing through the user's nose and mouth. Preferably, device 100 remains entirely within the user's mouth and all surfaces of device 100 that may contact the interior of the user's mouth are smooth to prevent injury or discomfort.

Device 100 includes an upper arch 10 adapted to receive at least some of a user's upper teeth and a lower arch 20 adapted to receive at least some of the user's lower teeth. Upper arch 10 and lower arch 20 may include molds of at least some of the user's upper and lower teeth, respectively, for improved fitting, performance, and comfort. In one embodiment, device 100 includes a positioning and adjustment mechanism 30 that couples lower arch 20 to upper arch 10, positions lower arch 20 vertically relative to upper arch 10, and may be adjusted to pull lower arch 20 forward to facilitate improved breathing. In a more particular embodiment, lower arch 20 may be precisely positioned vertically relative to upper arch 10 to precisely determine the opening of the user's lower jaw. As described more fully below, mechanism 30 may include an upper platform 40 coupled to upper arch 10, a lower platform 50 coupled to lower arch 20, and a hook 60 coupling upper platform 40 to lower platform 50. These components may be made from any suitable material, for example, a biocompatible metal or hard plastic.

FIGS. 2 through 5 illustrate more detailed views of example vertical positioning and forward adjustment mechanisms associated with mechanism 30. Hook 60 and lower platform 50 preferably have cooperating shapes to position lower arch 20 relative to upper arch 10. End 62 of hook 60 may snap, click, or otherwise lock into recess 52 of lower platform 50, such that suitable force is needed to remove end 62 from recess 52, or end 62 may be freely removable from recess 52. In one embodiment, the cooperating shapes of lower platform 50 and hook 60 precisely position lower arch 20 vertically relative to upper arch 10 to precisely determine an opening of the user's lower jaw. Hook 60 and lower platform 50 may be collectively referred to as a vertical positioning mechanism for lower arch 20. In one embodiment, a substantially rounded recess 52 formed in lower platform 50 acts as a socket to receive a substantially rounded end 62 of hook 60. Recess 52 of lower platform 50 is adapted to receive and position end 62 of hook 60 to pull lower arch 20 forward to facilitate improved breathing. Substantially rounded end 62 of hook 60 may be substantially spherical, as shown, or may have any other suitable substantially rounded shape. Use of the modifier "substantially" is intended to make it clear that true mathematical roundness, as in a true circle or sphere, is not required and that a substantially rounded end 62 or a substantially rounded recess 52 may have any suitable curved profiles. Furthermore, although a substantially rounded end 62 and a substantially rounded recess 52 are primarily described and may be preferred in certain circumstances, the present invention contemplates any suitable cooperating shapes for end 62 and recess 52 depending on the embodiment. Lower platform 50 may be fully integral to, permanently coupled to, or separate and removable from lower arch 20. Unless otherwise clear from the context, lower platform 50 may be deemed a part of lower arch 20, whether or not lower platform 50 is integral to lower arch 20, such that lower arch 20 may be said to include recess 52.

In one embodiment, hook 60 may be modified according to particular needs to provide increased flexibility. For example, the anterior portion of hook 60 may be lengthened or otherwise modified, either during or after initial construction of hook 60, to provide a support arm for the attachment of a suitable continuous positive airway pressure (CPAP) apparatus. As another example, flange 64 of hook 60 may be lengthened, either during or after initial construction of hook 60, such that the maximum forward adjustment of the lower jaw is increased. In one embodiment, hook 60 may be selected from among multiple interchangeable hooks 60 having different lengths of arm 61 to customize device 100 according to particular needs. Depending upon the length of arm 61 of the particular hook 60 selected, a corresponding precise opening of the user's lower jaw may be determined.

Figure 3:
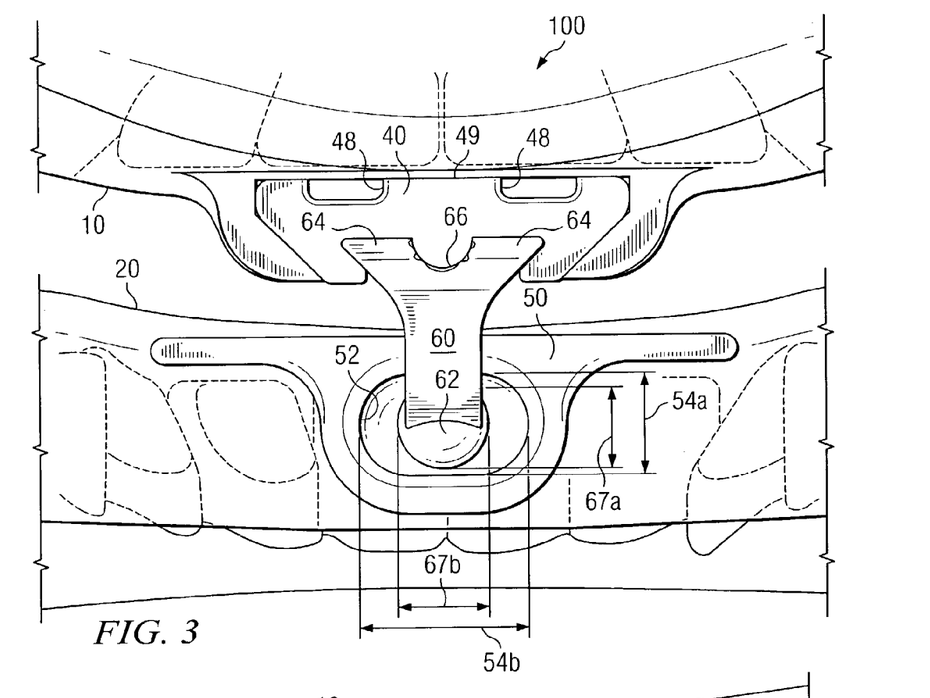
Figure 4:
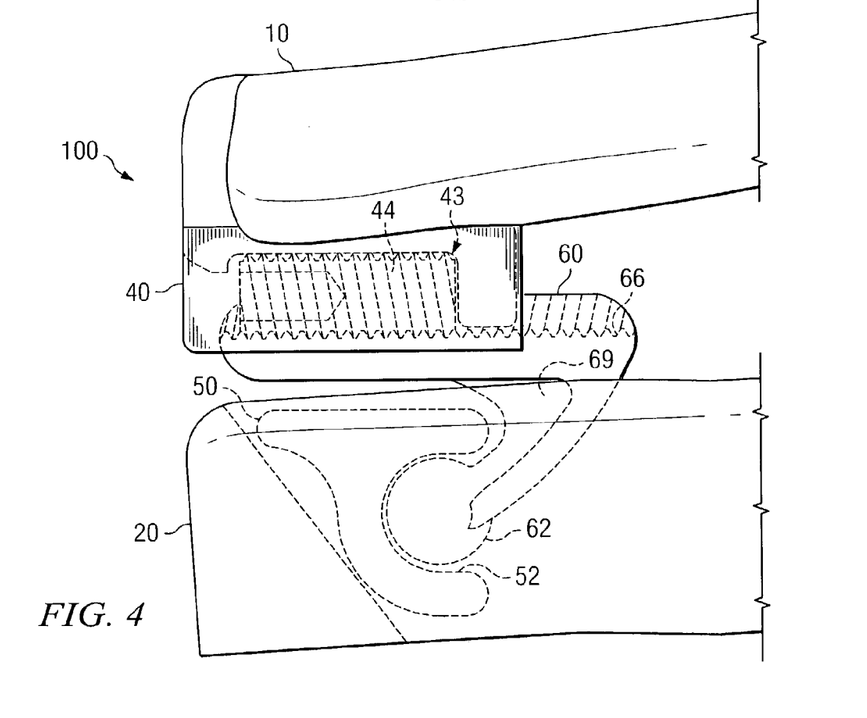

Referring to FIG. 3, in one embodiment a substantially rounded recess 52 of lower platform 50 is elongated such that substantially rounded recess 52 has a greater width than length, resulting in a substantially elliptical, ovular, or "pill" shape. In a particular embodiment, height 54a of substantially rounded recess 52 is slightly larger than height 67a of substantially rounded end 62 of hook 60, while width 54b of substantially rounded recess 52 is significantly larger than width 67b of substantially rounded end 62. Consequently, in this embodiment, lower platform 50, lower arch 20, and thus the user's lower jaw are permitted substantially more lateral freedom of movement than vertical freedom of movement, which may provide increased comfort without sacrificing performance associated with precise vertical positioning of lower arch 20. Similar elongation may be provided in embodiments in which end 62 and recess 52 are not substantially rounded. Where enhanced lateral freedom of movement for the lower jaw is not desired, any difference between widths 54b and 67b may be reduced. Of course, if no freedom of movement is desired vertically or laterally, then heights 54a and 67a or widths 54b and 67b, respectively, may be substantially equal. In one embodiment, a plate, strap, or other cover may be provided to secure end 62 in recess 52 to keep device 100 together during shipment, during use, between uses, or for any other suitable purposes.

Upper platform 40 may be fully integral to, permanently coupled to, or separate and removable from upper arch 10. For example, in one embodiment, upper arch 10 may include a slot to receive and engage upper platform 40 to couple upper platform 40 to upper arch 10, the slot and upper platform 40 having cooperating shapes. Although the slot of upper arch 10 and upper platform 40 are illustrated as being substantially triangular in shape along their sides, the slot of upper arch 10 and upper platform 40 may have any suitable cooperating shapes. Unless otherwise clear from the context, upper platform 40 may be deemed a part of upper arch 10, whether or not upper platform 40 is integral to upper arch 10.

In one embodiment, upper platform 40 may include a slot 42 to receive and engage a flange 64 of hook 60 to couple hook 60 to upper platform 40 and to allow forward and rearward adjustment of hook 60 to facilitate positioning of lower arch 20 and thus the user's lower jaw. Although slot 42 and flange 64 are illustrated as being substantially triangular in shape along their sides, slot 42 and flange 64 may have any suitable cooperating shapes.

In one embodiment, upper platform 40 includes a channel 43 that houses a threaded adjustor 44 and hook 60 includes a threaded channel 66 that engages the threads of adjustor 44. Adjustor 44 may be, for example, a threaded rod and may be made from any suitable material, for example, a biocompatible metal or hard plastic. Rotating adjustor 44, which is preferably prevented from moving forward or rearward within channel 43 using appropriate stops, causes hook 60 to move forwardly or rearwardly within slot 42 of upper platform 40.

Figure 5:
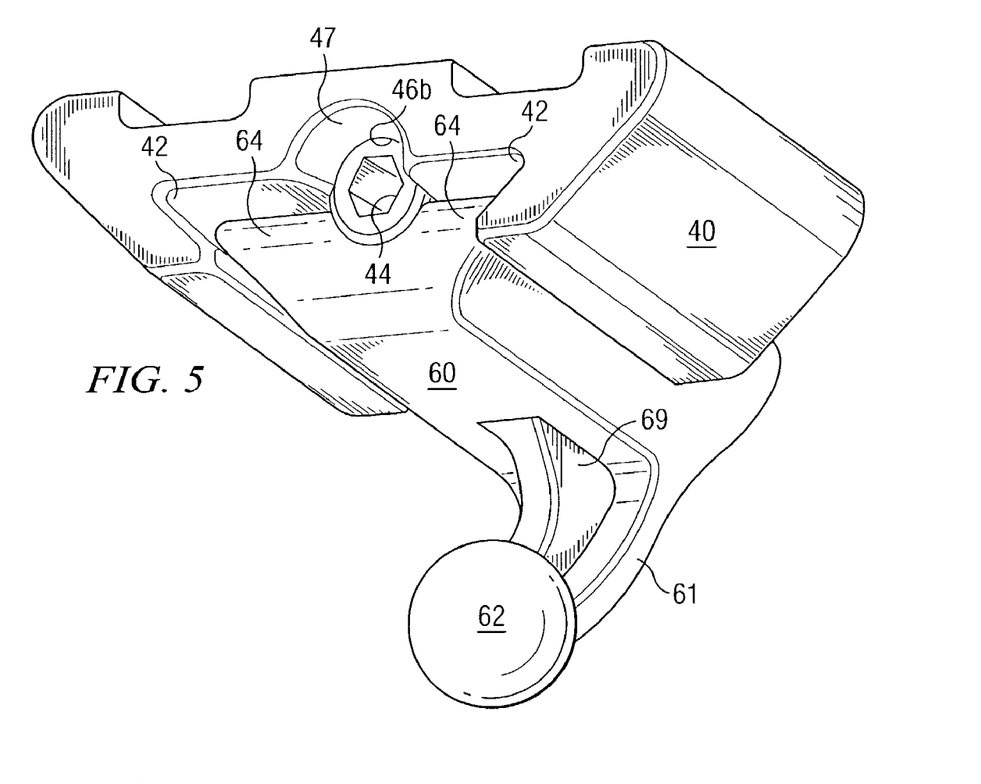

Referring to FIG. 5, in one embodiment upper platform 40 includes a stop 46b that substantially prevents adjustor 44 from moving forward when adjustor 44 is disposed in channel 43. A similar stop substantially preventing adjustor 44 from moving rearward is described below with reference to FIG. 7A. Upper platform 40 may include a depression 47 anterior to stop 46b to guide an Allen wrench or other suitable adjustment tool into a hexagonal or other recess formed in adjustor 44 to facilitate rotation of adjustor 44. Upper platform 40, adjustor 44, and hook 60 may be collectively referred to as a forward adjustment mechanism for lower arch 20.

The cooperating shapes of slot 42 of upper platform 40 and flange 64 of hook 60 permit forward and rearward travel of hook 60 within slot 42 while substantially preventing lateral and vertical movement of hook 60 relative to upper platform 40. Preferably, hook 60 is permitted to travel within slot 42 to any appropriate extent to adjust the extent to which lower arch 20, and thus the user's lower jaw, is pulled forward. For example, a portion of hook 60, including some or all of end 62, may be permitted to travel forward past the most anterior portion of upper platform 40 if desired, and a portion of hook 60, including some or all of end 62, may be permitted to travel rearward past the most posterior portion of upper platform 40 if desired, according to rotation of adjustor 44. However, as described more fully below, one or more stops may be provided to limit the forward and rearward travel of hook 60 within slot 42.

Figure 6A:
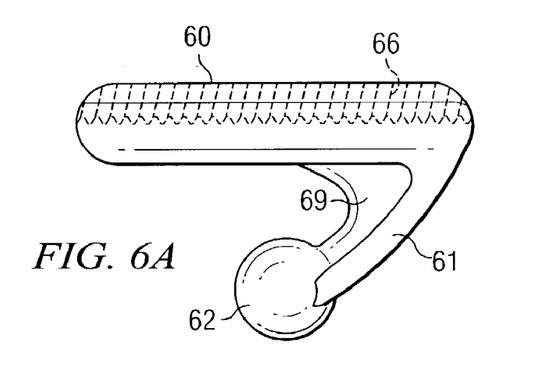
FIGS. 6A and 6B illustrate an example hook.
Figure 6B:
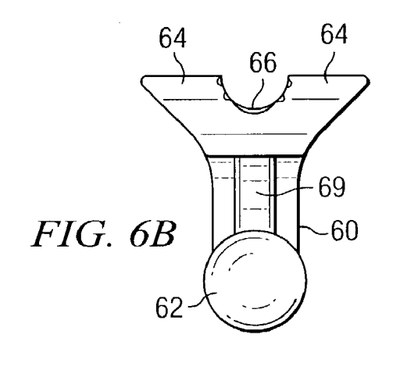
Figure 8A:
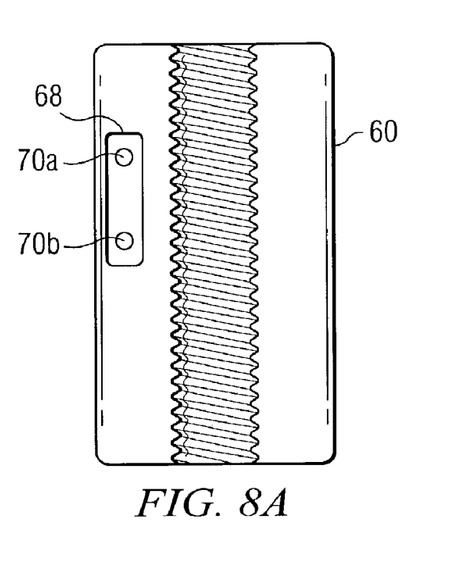
FIGS. 8A through 8C illustrate an example adjustment mechanism incorporating stops.

FIGS. 6A and 6B illustrate an example hook. In one embodiment, as described more fully below with reference to FIGS. 8A though 8C, one or more slots, cut-outs, or other elongated recesses 68 may be formed in flange 64 to contact one or more stops 70 that are positioned within upper platform 40 and made to extend into the one or more recesses 68 to limit the forward and rearward travel of hook 60 within slot 42 of upper platform 40. Hook 60 may include a flange 69 that provides additional strength to prevent deformation of hook 60 during use.

Figure 7A:
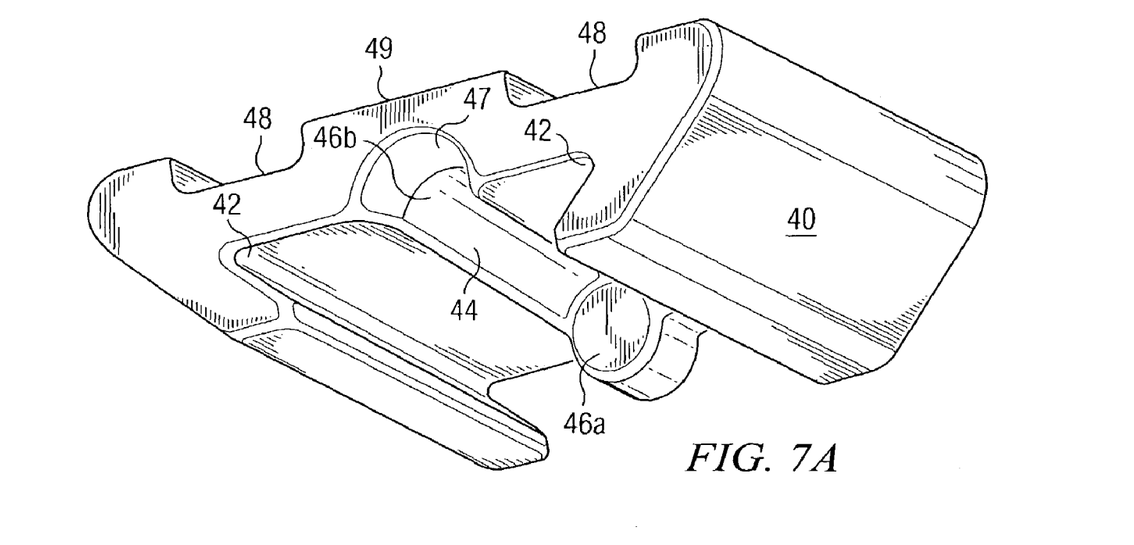
FIGS. 7A and 7B illustrate an example upper platform.
Figure 7B:
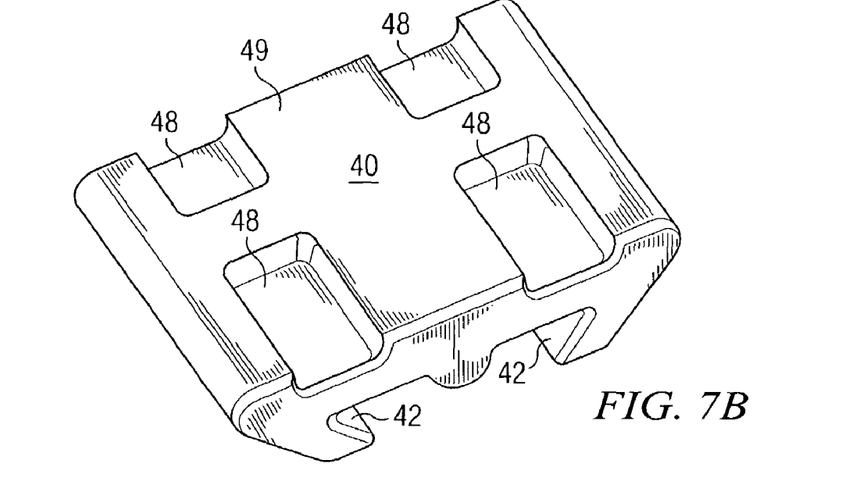

FIGS. 7A and 7B illustrate an example upper platform 40. As shown in FIG. 7A, in one embodiment channel 43, which houses threaded adjustor 44, is not threaded and adjustor 44 rotates freely within channel 43. Similar to stop 46b described above, stop 46a substantially prevents adjustor 44 from moving rearwardly when adjustor 44 is disposed in channel 43. As shown in FIG. 7B, in one embodiment upper platform 40 may include recesses 48 to receive a bonding material, such as an acrylic or adhesive, that helps couple upper platform 40 to upper arch 10. Middle portion 49 of upper platform 40 preferably adds additional thickness to upper platform 40 above adjustor 44 to provide strength.

Figure 8B:
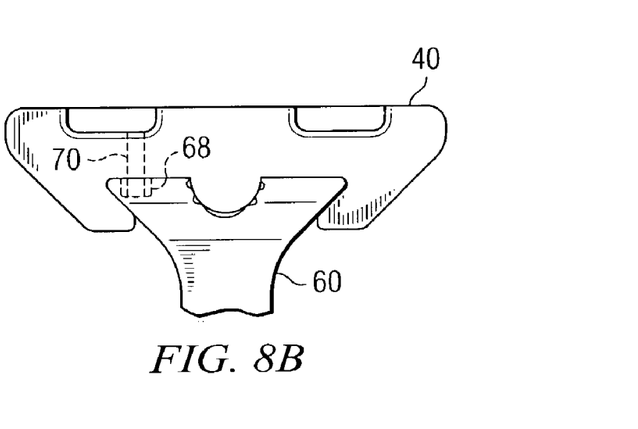
Figure 8C:
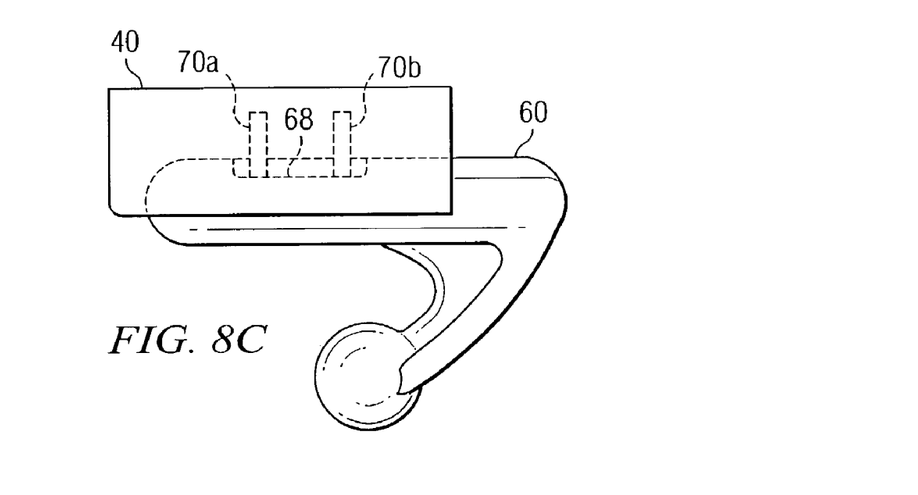

Referring to FIGS. 8B though 8C, in one embodiment, as described above, one or more stops 70 may be positioned within upper platform 40 and made to extend into one or more slots, cut-outs, or other elongated recesses 68 formed in flange 64 of hook 60 to limit the forward and rearward travel of hook 60 within slot 42. For example, stops 70 may be set screws placed in through-holes that are formed in upper platform 40. Either end of a recess 68 contacting a stop 70 will prevent further travel of hook 60 in a corresponding direction. In a particular embodiment, stops 70 may include a forward stop 70a for limiting the rearward travel of hook 60 within a single slot 42 and a rearward stop 70b for limiting the forward travel of hook 60 within the single slot 42. Although recess 68 is shown formed on the top of flange 64 of hook 60, recess 68 may be formed in any suitable location, for example, horizontally through either side of flange 64. Correspondingly, stops 70 may be positioned in any suitable location, for example, in throughholes formed in the sides of upper platform 40 to engage recess 68 formed horizontally through a side of flange 64.

Figure 9A:
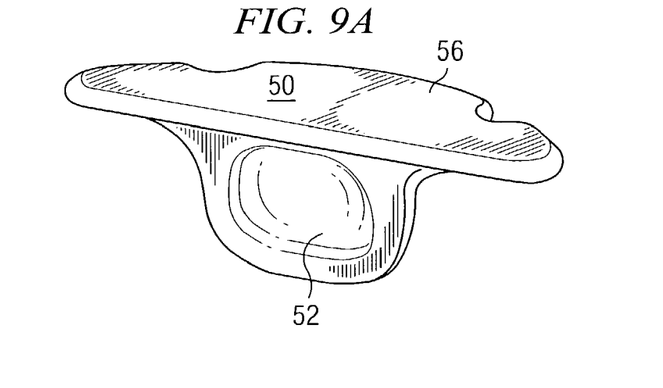
FIGS. 9A and 9B illustrate an example lower platform.
Figure 9B:
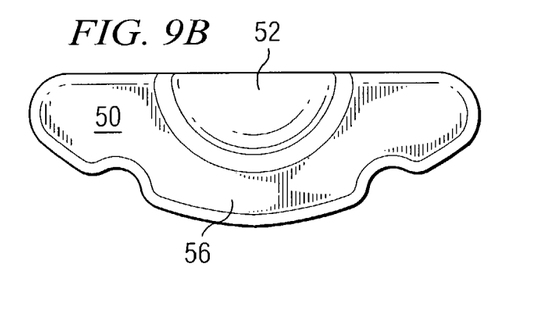

FIGS. 9A and 9B illustrate an example lower platform 50. In one embodiment, lower platform 50 includes a flat arched anterior portion 56 that seats on the user's lower anterior teeth, providing improved balance, decreased wear, and better overall comfort and performance.

Figure 10:
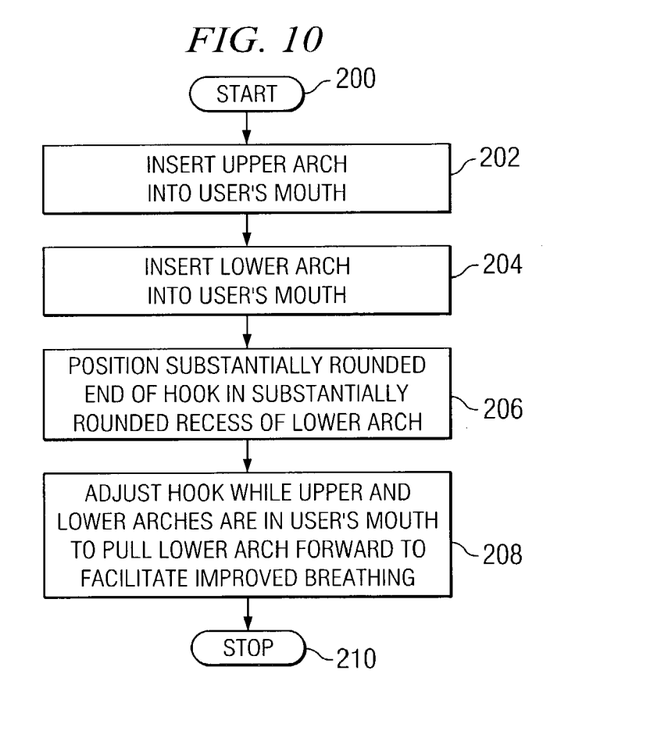
FIG. 10 illustrates an example method of improving a user's breathing.

FIG. 10 illustrates an example method of improving a user's breathing using device 100. The method begins at step 202, when upper arch 10 is inserted into the user's mouth. In one embodiment, upper arch 10 is adapted to receive at least some of the user's upper teeth and is coupled to hook 60 having a substantially rounded end 62. At step 204, lower arch 20 is inserted into the user's mouth. In one embodiment, lower arch 20 is adapted to receive at least some of the user's lower teeth, lower arch 20 having a substantially rounded recess 52 adapted to receive and position the substantially rounded end 62 of hook 60 to pull lower arch 20 forward to facilitate improved breathing. At step 206, the substantially rounded end 62 of hook 60 is positioned in the substantially rounded recess 52 of lower arch 20. At step 208, hook 60 is adjusted while upper arch 10 and lower arch 20 are in the user's mouth. As described above, although a substantially rounded end 62 and a substantially rounded recess 52 are primarily described and may be preferred in certain circumstances, the present invention contemplates any suitable cooperating shapes for end 62 and recess 52 depending on the embodiment.

Although an example method is described, the steps may be accomplished in any appropriate order. For example, inserting the upper and lower arches can be accomplished sequentially, in any order, or simultaneously. The present invention contemplates using methods with additional steps, fewer steps, or different steps, so long as the methods remain appropriate for improving a user's breathing.

Although the present invention has been described above in connection with several embodiments, it should be understood that numerous changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving a user's breathing, comprising:
   an upper arch adapted to receive at least some of the user's upper teeth, the upper arch having a midline that aligns substantially with the mesial plane of the user's mouth when the upper arch is inserted in the user's mouth;
   a hook coupled to the upper arch proximate the midline of the upper arch, the hook comprising a substantially rounded end having an anterior surface adapted to be directed in an anatomically anterior direction when the upper arch is inserted in the user's mouth; and
   a lower arch:
      adapted to receive at least some of the user's lower teeth;
      having a midline that aligns substantially with the mesial plane of the user's mouth when the lower arch is inserted in the user's mouth;
      having a lingual surface adapted to be positioned lingual to the user's lower teeth when the lower arch is inserted in the user's mouth; and
      comprising a substantially rounded recess in the lingual surface of the lower arch proximate the midline of the lower arch, the recess having a posterior surface adapted to be directed in an anatomically posterior direction when the lower arch is inserted in the user's mouth, the recess adapted to receive and position the substantially rounded end of the hook such that the anterior surface of the end of the hook contacts the posterior surface of the recess to pull the lower arch forward in the anatomically anterior direction to facilitate improved breathing.

2. The device of claim 1, wherein the substantially rounded recess of the lower arch is adapted to precisely position the substantially rounded end of the hook vertically relative to the upper arch to precisely determine an opening of the user's lower jaw.

3. The device of claim 1, wherein the substantially rounded end of the hook is substantially spherical.

4. The device of claim 1, wherein the substantially rounded recess comprises an elongated substantially rounded recess having a slightly larger height than the substantially rounded end of the hook and a significantly larger width than the substantially rounded end of the hook such that the lower arch is permitted substantially more lateral freedom of movement than vertical freedom of movement.

5. The device of claim 1, wherein:
   the hook comprises an arm having a length that determines an opening of the user's lower jaw; and
   the hook is selected from among multiple hooks having different arm lengths.

6. The device of claim 1, further comprising:
   an upper platform coupled to the upper arch, the upper platform comprising a slot adapted to receive and engage a flange of the hook, the slot further adapted to permit forward and rearward travel of the hook within the slot and to substantially prevent lateral and vertical movement of the hook relative to the upper platform; and
   a threaded adjustor disposed in a first channel formed in the upper platform, the adjustor adapted to engage a second threaded channel formed in the hook such that rotation of the adjustor causes the hook to travel forwardly or rearwardly within the slot.

7. The device of claim 6, wherein the upper platform further comprises a stop at each end of the first channel, the stops adapted to substantially prevent the adjustor from moving forwardly or rearwardly within the first channel.

8. The device of claim 6, wherein the adjustor comprises a screw having a recess adapted to receive an end of a tool for rotating the adjustor.

9. The device of claim 6, wherein the upper arch comprises a slot adapted to receive and engage the upper platform such that the slot and upper platform cooperate to substantially prevent movement of the upper platform within the slot of the upper arch.

10. The device of claim 6, further comprising one or more stops positioned in the upper platform and extending into a recess formed in the hook, the stops adapted to limit travel of the hook within the slot, an end of the recess formed in the hook contacting a stop preventing further travel of the hook within the slot in a corresponding direction.

11. The device of claim 10, wherein the one or more stops comprise a forward stop for limiting rearward travel of the hook within the slot and a rearward stop for limiting forward travel of the hook within the slot.

12. The device of claim 1, further comprising a lower platform coupled to the lower arch, the lower platform comprising the substantially rounded recess and a flat arched anterior portion that is forward of the substantially rounded recess and is adapted to seat on the user's lower anterior teeth.

13. A hook for a device for improving a user's breathing, wherein:
   the hook is adapted to be coupled to an upper arch of the device, the upper arch adapted to receive at least some of the user's upper teeth, the hook being adapted to be coupled to the upper arch proximate a midline of the upper arch that aligns substantially with the mesial plane of the user's mouth when the upper arch is inserted in the user's mouth;
   the hook comprises a substantially rounded end having an anterior surface adapted to be directed in an anatomically anterior direction when coupled to the upper arch and when the upper arch is inserted in the user's mouth;
   the hook is adapted to be received and positioned within a substantially rounded recess of a lower arch, the lower arch being adapted to receive at least some of the user's lower teeth, having a midline that aligns substantially with the mesial plane of the user's mouth when the lower arch is inserted in the user's mouth, and having a lingual surface adapted to be positioned lingual to the user's lower teeth when the lower arch is inserted in the user's mouth, the recess being in the lingual surface of the lower arch proximate the midline of the lower arch and having a posterior surface adapted to be directed in an anatomically posterior direction when the lower arch is inserted in the user's mouth, the anterior surface of the hook being adapted to contact the posterior surface of the recess to pull the lower arch forward in the anatomically anterior direction to facilitate improved breathing.

14. The hook of claim 13, wherein the substantially rounded end of the hook is substantially spherical.

15. The hook of claim 13, wherein:
the hook comprises an arm having a length that determines an opening of the user's lower jaw; and
the hook is selected from among multiple hooks having different arm lengths.

16. The hook of claim 13, further comprising:
a flange adapted to engage a slot of an upper platform coupled to the upper arch such that the hook is permitted to travel forwardly and rearwardly within the slot and is substantially prevented from moving laterally and vertically relative to the upper platform; and
a threaded first channel adapted to engage a threaded adjustor disposed in a second channel formed in the upper platform such that rotation of the adjustor causes the hook to travel forwardly or rearwardly within the slot.

17. The hook of claim 16, further comprising a recess adapted to contact one or more stops positioned in the upper platform and extending into the recess to limit travel of the hook within the slot, an end of the recess contacting a stop preventing further travel of the hook within the slot in a corresponding direction.

18. A lower platform for a device for improving a user's breathing, wherein:
the lower platform is adapted to be coupled to a lower arch of the device, the lower arch adapted to receive at least some of the user's lower teeth;
the lower platform has a midline that aligns substantially with the mesial plane of the user's mouth when the lower arch is inserted in the user's mouth;
the lower platform has a lingual surface adapted to be positioned lingual to the user's lower teeth when the lower arch is inserted in the user's mouth; and
the lower platform comprises a substantially rounded recess in the lingual surface proximate the midline:
the recess having a posterior surface adapted to be directed in an anatomically posterior direction when the lower platform is coupled to the lower arch and the lower arch is inserted in the user's mouth; and
the recess being adapted to receive and position a substantially rounded end of a hook coupled to an upper arch of the device proximate a midline of the upper arch, which aligns substantially with the mesial plane of the user's mouth when the upper arch is inserted in the user's mouth to pull the lower arch forward in an anatomically anterior direction to facilitate improved breathing.

19. The lower platform of claim 18, wherein the substantially rounded recess is adapted to precisely position the substantially rounded end of the hook vertically relative to the upper arch to precisely determine an opening of the user's lower jaw.

20. The lower platform of claim 18, wherein the substantially rounded recess comprises an elongated substantially rounded recess having a slightly larger height than the substantially rounded end of the hook and a significantly larger width than the substantially rounded end of the hook such that the lower arch is permitted substantially more lateral freedom of movement than vertical freedom of movement.

21. The lower platform of claim 18, further comprising a flat arched anterior portion that is forward of the substantially rounded recess and is adapted to seat on the user's lower anterior teeth.

22. An upper platform for a device for improving a user's breathing, the upper platform adapted to be coupled to an upper arch of the device that is adapted to receive at least some of the user's upper teeth, the upper platform comprising:
a slot adapted to receive and engage a flange of a hook, the slot further adapted to permit forward and rearward travel of the hook within the slot and to substantially prevent lateral and vertical movement of the hook relative to the upper platform;
a first channel adapted to receive a threaded adjustor that is adapted to engage a second threaded channel formed in the hook such that rotation of the adjustor causes the hook to travel forwardly or rearwardly within the slot; and
a stop at each end of the first channel, the stops adapted to substantially prevent the adjustor from moving forwardly and rearwardly within the first channel.

23. The upper platform of claim 22, further comprising one or more stops adapted to extend into a recess formed in the hook, the stops further adapted to limit travel of the hook within the slot, an end of the recess formed in the hook contacting a stop preventing further travel of the hook within the slot in a corresponding direction.

24. The upper platform of claim 23, wherein the one or more stops comprise a forward stop for limiting rearward travel of the hook within the slot and a rearward stop for limiting forward travel of the hook within the slot.

25. The upper platform of claim 22, further comprising one or more recesses formed on an upper surface of the upper platform to facilitate coupling the upper platform to the upper arch.

26. The upper platform of claim 22, wherein the upper platform is adapted to engage a slot of the upper arch such that the upper platform and slot of the upper arch cooperate to substantially prevent movement of the upper platform within the slot of the upper arch.

27. An adjustment mechanism for adjusting a lower arch of a device for improving a user's breathing, the lower arch adapted to receive at least some of a user's lower teeth, the adjustment mechanism comprising:
a hook comprising a substantially rounded end;
an upper platform comprising a slot adapted to receive and engage a flange of the hook, the slot further adapted to permit forward and rearward travel of the hook within the slot and to substantially prevent lateral and vertical movement of the hook relative to the upper platform; and
a threaded adjustor disposed in a first channel formed in the upper platform, the adjustor adapted to engage a second threaded channel formed in the hook such that rotation of the adjustor causes the hook to travel forwardly and rearwardly within the slot.

28. The adjustment mechanism of claim 27, wherein:
the hook comprises an arm having a length that determines an opening of the user's lower jaw; and
the hook is selected from among multiple hooks having different arm lengths.

29. The adjustment mechanism of claim 27, wherein the upper platform further comprises a stop at each end of the first channel, the stops adapted to substantially prevent the adjustor from moving forwardly or rearwardly within the first channel.

30. The adjustment mechanism of claim 27, further comprising a screw having a recess adapted to receive an end of a tool for rotating the adjustor.

31. The adjustment mechanism of claim 27, further comprising one or more stops positioned in the upper platform and extending into a recess formed in the hook, the stops adapted to limit travel of the hook within the slot, an end of the recess formed in the hook contacting a stop preventing further travel of the hook within the slot in a corresponding direction.

32. The adjustment mechanism of claim 31, wherein the one or more stops comprise a forward stop for limiting rearward travel of the hook within the slot and a rearward stop for limiting forward travel of the hook within the slot.

33. A positioning mechanism for positioning a lower arch of a device for improving a user's breathing, the lower arch adapted to receive at least some of the user's lower teeth, the positioning mechanism comprising:
  a hook adapted to be coupled to an upper arch that is adapted to receive at least some of the user's upper teeth and has a midline that aligns substantially with the mesial plane of the user's mouth when the upper arch is inserted in the user's mouth, the hook adapted to be coupled to the upper arch proximate the midline of the upper arch, the hook comprising a substantially rounded end having an anterior surface adapted to be directed in an anatomically anterior direction when the upper arch is inserted in the user's mouth; and
  a lower platform adapted to be coupled to the lower arch, the lower platform having a midline that aligns substantially with the mesial plane of the user's mouth when the lower arch is inserted in the user's mouth and having a lingual surface adapted to be positioned lingual to the user's lower teeth when the lower arch is inserted in the user's mouth, the lower platform comprising a substantially rounded recess in the lingual surface proximate the midline:
    the recess having a posterior surface adapted to be directed in an anatomically posterior direction when the lower platform is coupled to the lower arch and the lower arch is inserted in the user's mouth; and
    the recess adapted to receive and position the substantially rounded end of the hook to pull the lower arch forward in an anatomically anterior direction to facilitate improved breathing.

34. The positioning mechanism of claim 33, wherein the substantially rounded recess of the lower platform is adapted to precisely position the substantially rounded end of the hook vertically relative to the upper arch to precisely determine an opening of the user's lower jaw.

35. The positioning mechanism of claim 33, wherein the substantially rounded recess comprises an elongated substantially rounded recess having a slightly larger height than the substantially rounded end of the hook and a significantly larger width than the substantially rounded end of the hook such that the lower arch is permitted substantially more lateral freedom of movement than vertical freedom of movement.

36. The positioning mechanism of claim 33, wherein:
  the hook comprises an arm having a length that determines an opening of the user's lower jaw; and
  the hook is selected from among multiple hooks having different arm lengths.

37. A method of improving a user's breathing, comprising:
  inserting an upper arch into the user's mouth, the upper arch adapted to receive at least some of the user's upper teeth, the upper arch having a midline that aligns substantially with the mesial plane of the user's mouth when the upper arch is inserted in the user's mouth, the upper arch coupled to a hook proximate the midline of the upper arch, the hook comprising a substantially rounded end having an anterior surface adapted to be directed in an anatomically anterior direction when the upper arch is inserted in the user's mouth;
  inserting a lower arch into the user's mouth, the lower arch:
    adapted to receive at least some of the user's lower teeth;
    having a midline that aligns substantially with the mesial plane of the user's mouth when the lower arch is inserted in the user's mouth;
    having a lingual surface adapted to be positioned lingual to the user's lower teeth when the lower arch is inserted in the user's mouth; and
    comprising a substantially rounded recess in the lingual surface of the lower arch proximate the midline of the lower arch, the recess having a posterior surface adapted to be directed in an anatomically posterior direction when the lower arch is inserted in the user's mouth, the recess adapted to receive and position the substantially rounded end of the hook such that the anterior surface of the end of the hook contacts the posterior surface of the recess to pull the lower arch forward in the anatomically anterior direction to facilitate improved breathing;
  positioning the substantially rounded end of the hook in the substantially rounded recess of the lower arch; and
  adjusting the hook while the upper and lower arches are in the user's mouth to pull the lower arch forward in the anatomically anterior direction to facilitate improved breathing.

38. The method of claim 37, wherein positioning the substantially rounded end of the hook in the substantially rounded recess of the lower arch comprises using the substantially rounded recess of the lower arch to precisely position the substantially rounded end of the hook vertically relative to the upper arch to precisely determine an opening of the user's lower jaw.

39. The method of claim 37, wherein the substantially rounded end of the hook is substantially spherical.

40. The method of claim 37, wherein the substantially rounded recess comprises an elongated substantially rounded recess having a slightly larger height than the substantially rounded end of the hook and a significantly larger width than the substantially rounded end of the hook such that the lower arch is permitted substantially more lateral freedom of movement than vertical freedom of movement.

41. The method of claim 37, wherein:
  the hook comprises an arm having a length that determines an opening of the user's lower jaw; and
  the hook is selected from among multiple hooks having different arm lengths.

42. The method of claim 37, wherein:
  the upper arch is coupled to an upper platform comprising a slot adapted to receive and engage a flange of the hook, the slot further adapted to permit forward and rearward travel of the hook within the slot and to substantially prevent lateral and vertical movement of the hook relative to the upper platform; and
  the method further comprises rotating a threaded adjustor disposed in a first channel formed in the upper platform, the adjustor adapted to engage a second threaded channel formed in the hook such that rotation of the adjustor causes the hook to travel forwardly or rearwardly within the slot.

43. The method of claim 37, wherein the method is performed by the user or a clinical professional.

44. A method for manufacturing a device for improving a user's breathing, comprising:
providing an upper arch adapted to receive at least some of the user's upper teeth, the upper arch having a midline that aligns substantially with the mesial plane of the user's mouth when the upper arch is inserted in the user's mouth;
providing a hook adapted to be coupled to the upper arch proximate the midline of the upper arch, the hook comprising a substantially rounded end having an anterior surface adapted to be directed in an anatomically anterior direction when the hook is coupled to the upper arch and the upper arch is inserted in the user's mouth; and
providing a lower arch:
adapted to receive at least some of the user's lower teeth;
having a midline that aligns substantially with the mesial plane of the user's mouth when the lower arch is inserted in the user's mouth;
having a lingual surface adapted to be positioned lingual to the user's lower teeth when the lower arch is inserted in the user's mouth; and
comprising a substantially rounded recess in the lingual surface of the lower arch proximate the midline of the lower arch, the recess having a posterior surface adapted to be directed in an anatomically posterior direction when the lower arch is inserted in the user's mouth, the recess adapted to receive and position the substantially rounded end of the hook such that the anterior surface of the end of the hook contacts the posterior surface of the recess to pull the lower arch forward in the anatomically anterior direction to facilitate improved breathing.

45. The method of claim 44, wherein the substantially rounded recess is adapted to precisely position the substantially rounded end of the hook vertically relative to the upper arch to precisely determine an opening of the user's lower jaw.

46. The method of claim 44, wherein the substantially rounded end of the hook is substantially spherical.

47. The method of claim 44, wherein the substantially rounded recess comprises an elongated substantially rounded recess having a slightly larger height than the substantially rounded end of the hook and a significantly larger width than the substantially rounded end of the hook such that the lower arch is permitted substantially more lateral freedom of movement than vertical freedom of movement.

48. The method of claim 44, wherein:
the hook is one of multiple hooks provided, each comprising an arm having a length that determines an opening of the user's lower jaw; and
the hook is selected from among the multiple hooks having different arm lengths.

49. The method of claim 44, further comprising:
providing an upper platform adapted to be coupled to the upper arch, the upper platform comprising a slot adapted to receive and engage a flange of the hook, the slot further adapted to permit forward and rearward travel of the hook within the slot and to substantially prevent lateral and vertical movement of the hook relative to the upper platform; and
providing a threaded adjustor adapted to be disposed in a first channel formed in the upper platform, the adjustor adapted to engage a second threaded channel formed in the hook such that rotation of the adjustor causes the hook to travel forwardly or rearwardly within the slot.

50. The method of claim 49, wherein the upper platform further comprises a stop at each end of the first channel, the stops adapted to substantially prevent the adjustor from moving forwardly or rearwardly within the first channel.

51. The method of claim 49, wherein the adjustor comprises a screw having a recess adapted to receive an end of a tool for rotating the adjustor.

52. The method of claim 49, further comprising providing one or more stops adapted to be positioned in the upper platform and to extend into a recess formed in the hook, the stops adapted to limit travel of the hook within the slot, an end of the recess formed in the hook contacting a stop preventing further travel of the hook within the slot in a corresponding direction.

53. The method of claim 52, wherein the one or more stops comprise a forward stop for limiting rearward travel of the hook within the slot and a rearward stop for limiting forward travel of the hook within the slot.

54. The method of claim 49, wherein an upper arch comprises a slot adapted to receive and engage the upper platform such that the slot and the upper platform cooperate to substantially prevent movement of the upper platform within the slot of the upper arch.

55. The method of claim 44, further comprising providing a lower platform adapted to be coupled to the lower arch, the lower platform comprising the substantially rounded recess and a flat arched anterior portion that is forward of the substantially rounded recess and is adapted to seat on the user's lower anterior teeth.

56. A device for improving a user's breathing, comprising:
an upper arch adapted to receive at least some of the user's upper teeth, the upper arch having a midline that aligns substantially with the mesial plane of the user's mouth when the upper arch is inserted in the user's mouth;
a lower arch:
adapted to receive at least some of the user's lower teeth;
having a midline that aligns substantially with the mesial plane of the user's mouth when the lower arch is inserted in the user's mouth;
having a lingual surface adapted to be positioned lingual to the user's lower teeth when the lower arch is inserted in the user's mouth; and
comprising a substantially rounded recess in the lingual surface of the lower arch proximate the midline of the lower arch, the recess having a posterior surface adapted to be directed in an anatomically posterior direction when the lower arch is inserted in the user's mouth; and
means for coupling the upper arch to the lower arch, the means for coupling positioned proximate the midline of the upper arch, the means for coupling comprising a substantially rounded end having an anterior surface that is adapted to be received and positioned within the substantially rounded recess of the lower arch such that the anterior surface of the end contacts the posterior surface of the recess to pull the lower arch forward in the anatomically anterior direction to facilitate improved breathing.

57. A device for improving a user's breathing, comprising:
- a hook comprising a substantially rounded end;
- an upper arch adapted to receive at least some of the user's upper teeth, the upper arch comprising:
  - a slot adapted to receive and engage a flange of the hook, the slot further adapted to permit forward and rearward travel of the hook within the slot and to substantially prevent lateral and vertical movement of the hook relative to the upper arch;
  - a threaded adjustor disposed in a first channel formed in the upper arch, the adjustor adapted to engage a second threaded channel formed in the hook such that rotation of the adjustor causes the hook to travel forwardly or rearwardly within the slot; and
  - one or more stops positioned in the upper arch and extending into a recess formed in the hook, the stops adapted to limit travel of the hook within the slot, an end of the recess formed in the hook contacting a stop preventing further travel of the hook within the slot in a corresponding direction; and
- a lower arch adapted to receive at least some of the user's lower teeth, the lower arch comprising an elongated substantially rounded recess adapted to receive and position the substantially rounded end of the hook to pull the lower arch forward to facilitate improved breathing, the substantially rounded recess of the lower arch adapted to precisely position the substantially rounded end of the hook vertically relative to the upper arch to precisely determine an opening of the user's lower jaw, the elongated substantially rounded recess having a slightly larger height than the substantially rounded end of the hook and a significantly larger width than the substantially rounded end of the hook such that the lower arch is permitted substantially more lateral freedom of movement than vertical freedom of movement.

* * * * *

UNITED STATES PATENT AND TRADEMARK OFFICE
CERTIFICATE OF CORRECTION

PATENT NO. : 7,174,895 B2  Page 1 of 1
APPLICATION NO. : 10/428904
DATED : February 13, 2007
INVENTOR(S) : Thornton et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 65 days Delete the phrase "by 65 days" and insert -- by 99 days--

Signed and Sealed this

Thirtieth Day of October, 2007

JON W. DUDAS
*Director of the United States Patent and Trademark Office*